United States Patent [19]
Johnson et al.

[11] Patent Number: 5,372,785
[45] Date of Patent: Dec. 13, 1994

[54] SOLID-STATE MULTI-STAGE GAS DETECTOR

[75] Inventors: Christy L. Johnson, Essex Junction; Stephen L. Silverman, So. Burlington, both of Vt.

[73] Assignee: International Business Machines Corporation, Armonk, N.Y.

[21] Appl. No.: 115,949

[22] Filed: Sep. 1, 1993

[51] Int. Cl.$^5$ ............................................. G01N 27/04
[52] U.S. Cl. ...................................... 422/90; 422/88; 422/98; 73/31.02; 338/34
[58] Field of Search ..................... 422/83, 86, 88, 90, 422/93, 98; 73/31.05, 31.06, 31.02, 31.03; 338/34

[56] References Cited

U.S. PATENT DOCUMENTS

| | | | |
|---|---|---|---|
| 3,847,552 | 11/1974 | Hobgood et al. | 422/86 |
| 4,058,368 | 11/1977 | Svensson et al. | 23/254 |
| 4,169,369 | 10/1979 | Chang | 73/23 |
| 4,224,280 | 9/1980 | Takahama et al. | 422/98 |
| 4,324,761 | 4/1982 | Harris | 422/98 |
| 4,343,768 | 8/1982 | Kimura | 422/97 |
| 4,423,407 | 12/1983 | Zuckerman | 338/34 |
| 4,457,161 | 7/1984 | Iwanaga et al. | 73/23 |
| 4,574,264 | 3/1986 | Takashashi et al. | 338/34 |
| 4,584,867 | 4/1986 | Forster | 73/23 |
| 4,706,493 | 11/1987 | Chang et al. | 73/23 |
| 4,931,851 | 6/1990 | Sibbald et al. | 357/25 |
| 4,953,387 | 9/1990 | Johnson et al. | 73/25.03 |
| 5,071,768 | 12/1991 | Klodowski | 436/39 |
| 5,145,645 | 9/1992 | Zakin et al. | 422/98 |
| 5,250,170 | 10/1993 | Yagawara et al. | 204/431 |

OTHER PUBLICATIONS

Andrew et al., "Hydrogen Permeation Through Copper-Coated Palladium", J. Appl. Physics, 70(7), pp. 3600–3604, Oct. 1991.
Fare et al., "Quasi-Static and High Frequency C(V)-Response of Thin Platinum Metal-Oxide-Silicon Structures to Ammonia", Sensor and Actuators, 14, pp. 369–386, 1988.
Jelley et al., "A Dual-Mechanism Solid-State Carbon-Monoxide and Hydrogen Sensor Utilizing an Ultrathin Layer of Palladium", IEEE Trans. on Electron Device, vol. ED-34, No. 10, pp. 2086–2097, Oct. 1987.
Maclay et al., "The Response of MOS Sensors with Ultrathin Palladium Gates to Carbon Monoxide and Methane", Sensors and Actuators, 14, pp. 331–348, 1988.

Primary Examiner—Jeffrey R. Snay
Assistant Examiner—Long V. Le
Attorney, Agent, or Firm—Heslin & Rothenberg

[57] ABSTRACT

A solid-state, multi-stage gas detector for detecting a selected gaseous species from a plurality of gaseous species. The multi-stage gas detector includes a first conductive layer, exposable to the plurality of gaseous species, which permits the selected gaseous species to diffuse therethrough and which interacts with at least one of the plurality of gaseous species such that its conductivity changes. A second conductive layer, electrically isolated from the first conductive layer, interacts with the selected gaseous species after it has passed through the first conductive layer such that the second conductive layer's conductivity changes in relation thereto. Electrodes are attached to the first conductive layer and to the second conductive layer for separate detection of conductivity changes within the conductive layers. Detector conductivity changes comprise detection information correlated to the selected gaseous species. Multiple gaseous species may be concurrently detected by the multi-stage detector through appropriate selection of conductive layers for a given environment.

19 Claims, 2 Drawing Sheets

SOLID-STATE MULTI-STAGE GAS DETECTOR

TECHNICAL FIELD

This invention relates in general to gas sensors, and more particularly, to solid-state gas detectors of a type suitable for monitoring a plurality of gases within an enclosure.

BACKGROUND ART

Gas sensors are useful for performing a variety of functions, and find application in many industries, including semiconductor fabrication, automotive, pharmaceutical, chemical, health care and environmental technologies. In all these industries, the common need is for an inexpensive, sensitive, selective and reliable gas sensor for detecting (and quantifying) one or more gaseous contaminants. The following discussion focuses on detection issues for the semiconductor fabrication industry, but the solid-state detector disclosed has application in all of the noted industries.

As feature size and overlay tolerances of semiconductor products continue to shrink, the impact of gaseous and particulate contamination increases. Herein the focal point is contamination within a wafer enclosure used, for example, to transport and/or hold wafers between processes. Of primary concern is film outgassing. In the case of resist-coated wafers, low vapor pressure gases are released over time at room temperature. These gaseous species can be adsorbed or absorbed on the wafers, they can diffuse through other films on a wafer, they can be adsorbed on enclosure walls, or they can leave behind precipitates anywhere within the enclosure including on the wafers. Over time, these residuals accumulate and the process can reverse such that gaseous and particulated materials can travel, for example, from an enclosure's walls to wafers within the enclosure.

Monitoring such contamination is complex. Considerations for each application include reliability, sensitivity, selectivity, installation and operation convenience, and cost. Ideally, every wafer enclosure will someday contain a detector continuously monitoring to detect extremely small quantities of materials of interest without interference from other species and yet be easy in operation to use and require minimal or no maintenance. The parametric field for such a detector is extensive; with possible contributions from gas residuals, precipitates from the gas phase, and particulation to the overall level of contamination.

One known approach to monitoring contamination levels is to employ an analytical detection technique, such as mass spectrometry, IR, and/or microbalance measuring. Such techniques, which are well described in the art, are generally expensive, cumbersome and are not in-situ or intended to function as a continuous monitor. Another approach to monitoring contamination levels is to employ a solid-state detector.

Various solid-state gas detectors are described in the open literature. For example, many prior art devices are based on semiconductor films, such as tin oxide (e.g., see U.S. Pat. Nos. 4,706,493 or 4,169,369). These films typically involve surface adsorption, diffusion of the gas through the bulk of the film, and finally an electrical response. Further, it has been proposed to mount a plurality of semiconductor thin films on a common substrate in a two-dimensional grid such that all films are in contact with the unknown gas and different films in the grid detect interference due to different gaseous species. Most solid-state detectors, however, have one or more disadvantages associated therewith, including low sensitivity (i.e., inability to detect gas of interest at desired concentration level), low selectivities (i.e., fail to detect a gas of interest in the presence of other gases), long-term drift, hysteresis effects, limited range of detectable gases, limited range of operating temperature and/or slow response time.

Accordingly, there exists a need in many industries for an enhanced solid-state gas detector (suitable, e.g., for monitoring contamination within an enclosure) having improved reliability, sensitivity, selectivity, installation and operation convenience, and a lower cost. The present invention provides such a solid-state gas detector.

DISCLOSURE OF INVENTION

Briefly summarized, this invention comprises in one aspect a solid-state, multi-stage gas detector for detecting at least one selected gaseous species present in a plurality of gaseous species within an environment. The multi-stage gas detector includes a first conductive layer exposable to the environment having the plurality of gaseous species. This first conductive layer permits the at least one selected gaseous species to diffuse therethrough and interacts with at least one of the plurality of gases within the environment such that conductivity thereof changes in response thereto. A second conductive layer is electrically isolated from the first conductive layer but is disposed to receive the at least one selected gaseous species after diffusing through the first conductive layer. This second conductive layer chemically interacts with the at least one selected gaseous species such that conductivity thereof changes in response thereto. Electrodes are electrically attached to the first conductive layer and to the second conductive layer for separately detecting conductivity change in the first conductive layer and conductivity change in the second conductive layer. These conductivity changes represent (at least in part) detection information for the at least one selected gaseous species. Numerous detector enhancements are described and claimed.

In one enhanced embodiment, the second conductive layer is disposed at least partially beneath the first conductive layer to facilitate receiving of the at least one selected gaseous species diffusing through the first conductive layer. An electrical insulating layer is disposed between the first conductive layer and the second conductive layer to electrically isolate the two layers. The electrical insulating layer is at least semi-permeable such that the at least one selected gaseous species diffusing through the first conductive layer passes through the electrical insulating layer to the second conductive layer. In further embodiments, one or more additional conductive layers may be added for the detection of multiple selected gaseous species. In each embodiment of the invention, however, multiple partition stages are employed.

A solid-state detector pursuant to the present invention has numerous advantages over heretofore known solid-state gas detection units. A solid-state, multi-stage gas detector in accordance with the invention is suitable for monitoring contamination with an improved reliability, sensitivity, selectivity, and installation and operation convenience, in comparison with previous gas detectors. In one application, the detector is particularly suited for monitoring contamination within wafer transport and storage enclosures used in the semiconductor industry. Every wafer enclosure could have a detector in accordance with the invention continuously monitoring to detect small quantities of pre-identified contaminants without interference from other gaseous species within the enclosure. A detector pursuant to the invention is easy to use and requires minimal or no maintenance. Applications for the multi-stage gas detector can be found in the semiconductor industry, along with the automotive, pharmaceutical and chemical industries, and the health care and environmental fields.

BRIEF DESCRIPTION OF DRAWINGS

These and other objects, advantages and features of the present invention will be more readily understood from the following detailed description of certain preferred embodiments of the present invention, when considered in conjunction with the accompanying drawings in which.

BEST MODE FOR CARRYING OUT THE INVENTION

As can be understood from the following discussion, a multi-stage gas detector in accordance with the present invention can be implemented in any one of multiple ways. The embodiments depicted and described herein are provided by way of example only and should not be interpreted to limit the scope of the claims appended herewith.

Figure 1:
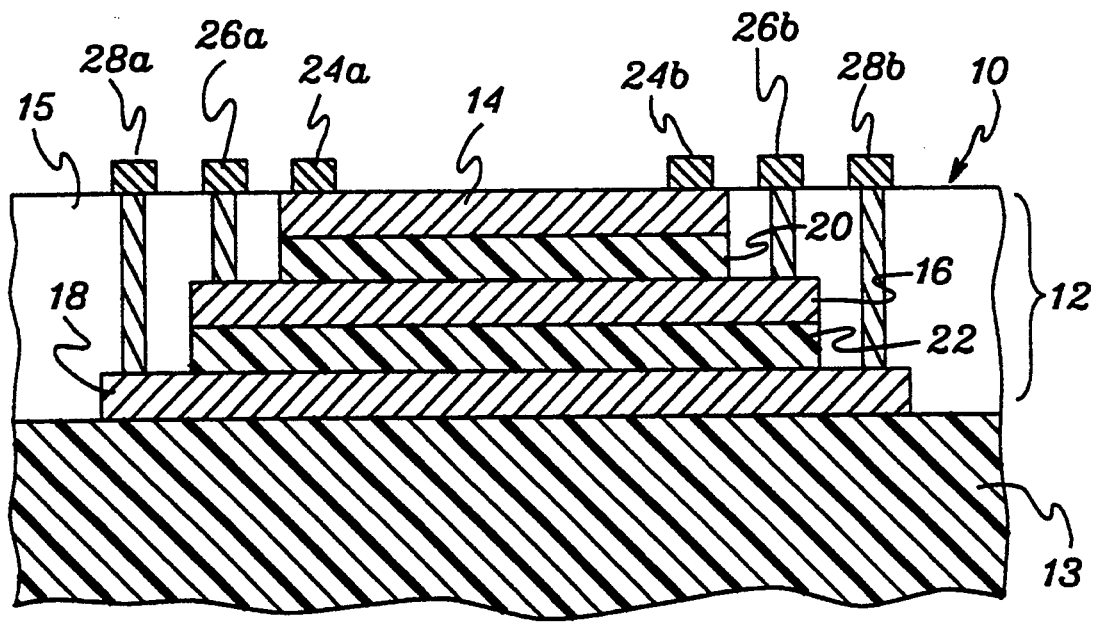
FIG. 1 is a cross-sectional view of one embodiment of a solid-state gaseous species detector pursuant to the present invention.

A first embodiment of a multi-stage gas detector, generally denoted 10, pursuant to the present invention is depicted in FIG. 1 (not drawn to scale). In this embodiment, the solid-state, multi-stage gas detector has three conductive layers 12 in a stacked, pyramidal configuration disposed above a supporting substrate 13. These layers are aligned such that a first conductive layer 14 is disposed above a second conductive layer 16, which is disposed above a third conductive layer 18. Conductive layer 16 extends in a horizontal plane further than conductive layer 14 to ensure that all gases diffusing through conductive layer 14 impinge upon conductive layer 16, while conductive layer 18 extends in a horizontal plane further than second conductive layer 16 to similarly ensure that all gases diffusing through layer 16 reach third conductive layer 18. The result is a pyramidal configuration which, although practical, comprises only one embodiment of the present invention. Further, one or more additional conductive layers may be added to the stack as needed. Fabrication of conductive layers 12 in a stacked, pyramidal configuration above supporting substrate 13 can be accomplished using conventional semiconductor manufacturing techniques. For example, chemical vapor deposition, evaporation or sputtering of conductive films can be employed depending upon the particular film and desired thickness. Conventional mask and etch processes could be used to define the pyramidal configuration (or other desired configuration).

The conductive layers are electrically isolated by appropriately configured and sized insulating layers, such as first electrical insulating layer 20 and second electrical insulating layer 22. Further, the outer edges of the conductive layers are preferably surrounded by an appropriate insulator 15 impervious to gaseous species diffusion. These layers and the surrounding insulator can be formed via conventional semiconductor fabrication techniques. For example, insulator 15 may be conformally fabricated in a plasma enhanced CVD process. As shown, insulating layer 20 is disposed between first conductive layer 14 and second conductive layer 16, while second insulating layer 22 is disposed between second conductive layer 16 and third conductive layer 18. Electrical contact to conductive layers 14, 16 & 18 is made by electrode pairs 24a, 24b, 26a, 26b, 28a, 28b, respectively. In addition to a sensing operation, the electrode pairs also function as a conduit for the application of power to the respective conductive layers. If desired, however, additional electrodes may be employed. For example, it may be convenient to establish an electrical current through a conductor via one set of electrodes and measure conductivity changes within the conductive layer via a second set of electrodes.

Figure 3:
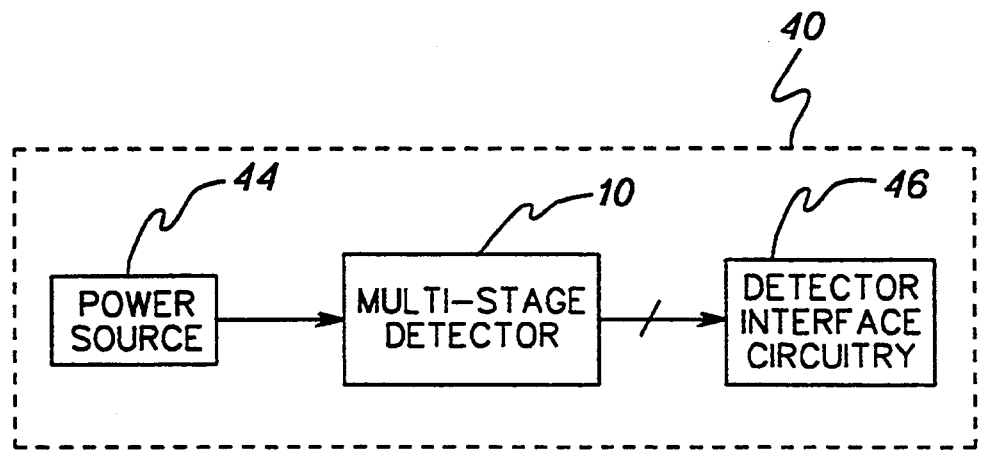
FIG. 3 is a simplified circuit diagram of a detection unit pursuant to the present invention.

FIG. 3 is a block diagram schematic of a completed detection unit pursuant to the present invention. The unit, disposed within an enclosure 40 (shown in phantom), includes a multi-stage detector, such as detector 10, coupled to receive energy from a power source 44 and provide conductivity readings to a detector interface circuit 46. Various embodiments of power source 44 and detector interface circuit 46 are available to those skilled in the art based upon the description provided herein and the state of the art.

In the present invention, the diffusive properties of contaminants within an enclosed environment to which the detector is exposed are used by differing film materials (i.e., the different conductive layers) to discriminate between gaseous species present within the environment. The multi-layer structure is uniquely tailored to each application to allow or prevent gaseous diffusion based on the chemistry of the gaseous species to be sensed. Detection is based on conductivity change due to the addition or removal of a gaseous species. As used herein, "gaseous species" means a gaseous element or compound, including organic and inorganic compositions. The individual conductive layers involved in species separation are electrically isolated so that different information is collected at the different levels, thereby enhancing the ability of a multi-stage gas detector pursuant to the invention to discriminate between gaseous species.

Part of the layering concept involves the selection and placement of electrically insulating layers between the transducing films, and in any exterior contact region. These insulating layers are preferably permeable or semi-permeable in nature within the multi-layer structure, with diffusion barriers (such as silicon nitride or other nitrides) in the exterior region(s) depending upon the species to be sensed. Thus, some layers may allow the serial progression of gaseous species through the structure whereas others operate to prevent diffusion in areas where gas could, for example, enter the structure laterally, thereby circumventing the multiple partition staging.

A variation of the basic structure is to photolithographically define separate detection areas with differing layers and layer combinations. An aspect of the gas detector's serial nature is that it acts as a filter and concurrently allows gas detection at distinct stages in the partitioned structure. Note that diffusion is time dependent but that this is less of a consideration in this semiconductor application since monitoring is assumed to be done over an extended time period. Further, monitoring can be either continuous or intermittent depending upon the given application.

Figure 2:
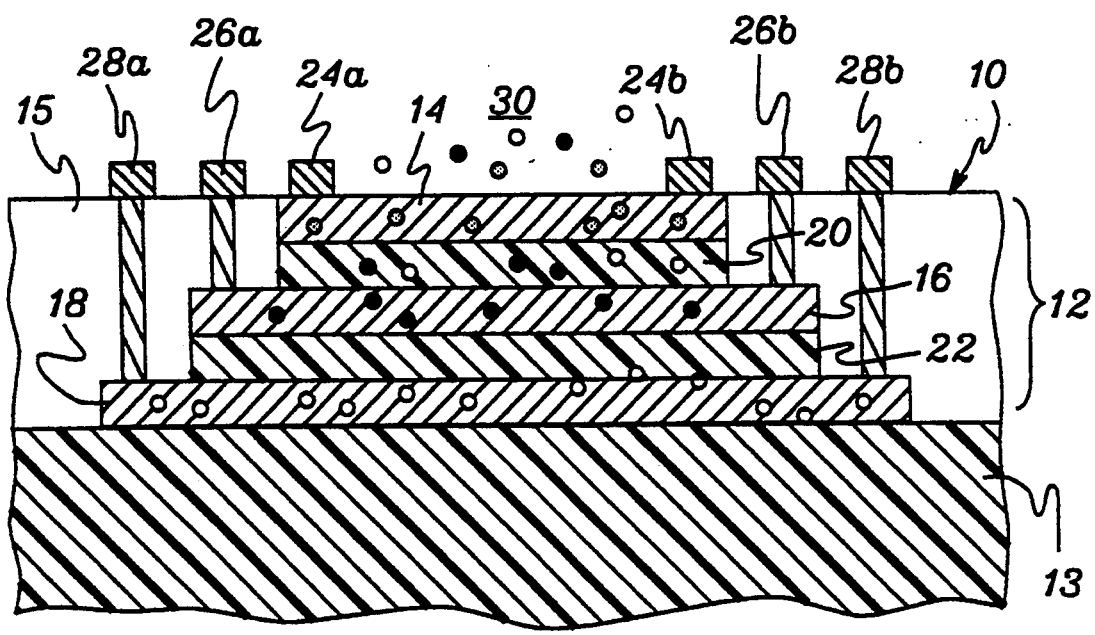
FIG. 2 is a cross-sectional view of the detector of FIG. 1 exposed to an environment having a plurality of gaseous species.

FIG. 2 depicts multi-stage gas detector 10 in monitoring use within an environment containing three selected gaseous species, generally denoted 30, for which the detector is predesigned to sense, i.e., the layers are respectively predefined to chemically react with at least one of the subject gaseous species. After a sufficient period of time, a first type of gaseous species (gray-shaded circles) is shown to diffuse into conductive layer 14, but not through this first layer. Only the second and third type of gaseous species (black-shaded and white-shaded circles, respectively) are allowed to pass through the first conductive layer into first insulating layer 20, and from there into second conductive layer 16 and, in the case of the third type of gaseous species, subsequently into third conductive layer 18. Note that the second selected gaseous species (black-shaded circles) is shown to pass into second conductive layer 16 but not through this layer. Thus, based on the assumed filtering functions of the first conductive layer and the second conductive layer, a vertical separation of gaseous species diffusing into the detector is achieved. This separation means that each conductive film receives a unique combination of gaseous species. Note further that if a gaseous species does not interact electrically with a conductive film, either individually or in combination with other gaseous species, then there is no need to filter the gaseous species from reaching the particular conductive film. Such species would essentially be ignored by the conductive film.

In accordance with the present invention, each conductive film is preselected for a particular application to ensure a conductivity change with a changing concentration of a selected gaseous species. Film conductivity changes arise from chemical interactions wherein a gaseous species is adsorbed or absorbed, or diffused through the film. The materials employed for the conductivity layers include ultra-thin metal films, polymetric materials (especially those of a similar nature to the photoresist employed), dielectric materials and zeolites, which can filter molecules based on their size distribution. Certain metals may be employed to deliberately prevent the passage of contaminants, while other materials may be employed to allow diffusion. The diffusive properties of the contaminants with respect to the differing film materials is used to discriminate between gaseous species.

Note that the thicknesses of the interspersed electrical insulating layers (20 & 22) must be such as to allow for diffusion of selected gaseous species therethrough. If desired, one or more of these insulating layers could also be chosen to function as a filter to prevent diffusion of unwanted gaseous species into subsequent conductive layers of the serially coupled multi-stage gas detector.

By way of example, hydrogen ($H_2$) gas is known to diffuse through palladium (Pd) metal but does not diffuse through other metals, such as copper (Cu). Thus, if desirable to have hydrogen continue diffusing through the structure, a Pd layer might be chosen, but if hydrogen is an interfering gas as it diffuses through the structure, a different metal such as Cu might be chosen. Building upon this principal, if a succession of materials is placed in series (see FIG. 1), with a first conductive layer allowing multiple species to travel through it, a second conductive layer allowing fewer species to pass and so forth, separation of material is achieved.

By way of general guidance, there are a number of factors to be considered in selecting materials for a multiple partition staged structure in accordance with the present invention. These factors include: the expected field of gaseous species; the possible field of gaseous species; sensitivity and selectivity requirements; the range of temperatures in the testing environment; whether a cumulative measurement or an instantaneous measurement is desired; adhesion of the films to one another; diffusion properties of the gaseous species of interest; known interactions between gaseous species and selected films; and consideration of whether the detector itself could contaminate its environment based upon the materials selected.

Figure 4:
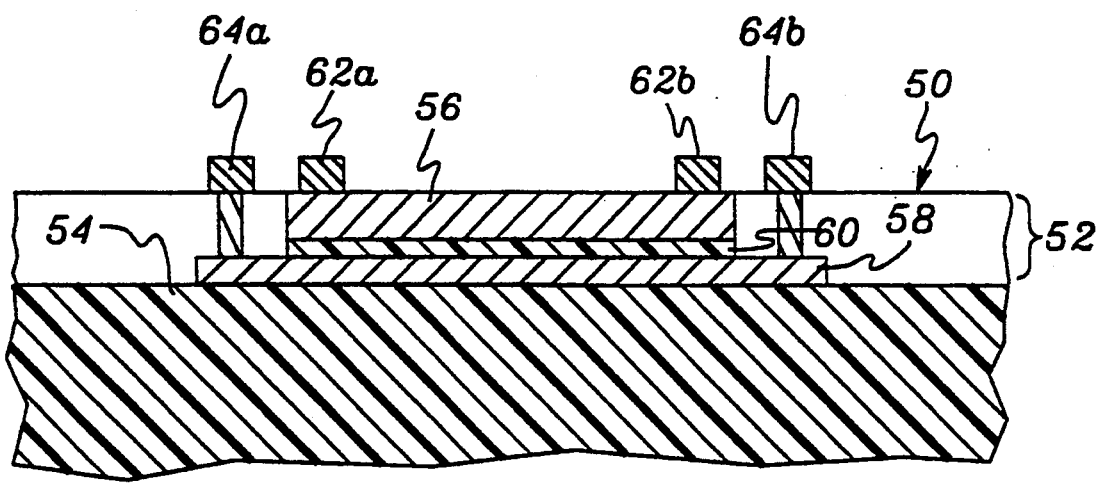
FIG. 4 is a cross-sectional view of another embodiment of a solid-state gaseous species detector pursuant to the present invention.

Another embodiment of a multi-stage gas detector pursuant to the present invention, generally denoted 50, is shown in cross-sectional view in FIG. 4. In this embodiment, two conductive layers comprise a multi-stage stack structure 52, which is disposed upon a substrate 54. Stack structure 52 includes a first conductive layer 56 disposed above a second conductive layer 58 and is electrically isolated therefrom by an appropriate insulating film 60. Electrodes 62a and 62b contact first conductive layer 56, while electrode pair 64a & 64b makes contact to second conductive layer 58. (Although somewhat proportional, the layers are not drawn to scale.)

As a specific example of this embodiment, assume that first conductive layer 56 comprises palladium metal (Pd), insulating layer 60 is silicon nitride and second conductive layer 58 is platinum (Pt). The staging is located on a silicon substrate 54. The uppermost layer, i.e., the palladium metal (Pd) layer, is permeable to hydrogen (and to a lesser degree to other gases such as ammonia) such that it may readily be used as a hydrogen filter. Layer 60 is an insulator, such as silicon nitride, which is thick enough to electrically isolate but thin enough to allow diffusion (e.g., 20-100 Angstroms may be an appropriate range). Should layer 60 comprise a thick film of nitride, then a diffusion barrier for most gases will exist even at high temperatures. If there is indeed hydrogen present, the gas will pass through first conductive layer 56 and insulating layer 60 for sensing at platinum (Pt) layer 58.

If there are adhesion problems between platinum and the nitride so as to affect device performance, a different film such as chromium (Cr) or titanium (Ti) might be used instead of platinum. Operating temperatures would typically be in the room temperature to approximately 600° C. range. Various concentration of gases could be resolved by selection of differing film thicknesses.

Those skilled in the art will recognize that the present invention can be employed with gas sensing material where the selected gaseous species contributes electrons to the sensing material or where the selected gaseous species withdrawals electrons from the sensing material. Again, the object is to select a material which will have a conductivity change in the presence of a selected gaseous species. A simple example of this is hydrogen ($H_2$) and platinum (Pt), and Oxygen ($O_2$) and platinum (Pt). In the case of hydrogen, hydrogen contributes electrons and causes the resistance of the platinum conductive layer to decrease. This resistance change is even more pronounced if the platinum is partially oxidized. With an $O_2$—PT combination, the opposite occurs such that electrons are withdrawn by the oxygen, thereby increasing resistance of the conductive layer. The two are not perfectly parallel, however, because the $H_2$—Pt interaction is typically irreversible (with a change usually occurring because hydrogen reduces the oxidation stage of the platinum). The $O_2$—Pt interaction can be set up such that it is fully reversible.

Detector responsivity might be recovered via high temperature treatment after long term sensing is finished, but most applications of a layered-type detector pursuant to the present invention are anticipated to be for one time use. The concept of withdrawing versus contributing electrons still applies, i.e., a conductivity change correlates to the presence of a gaseous species of interest.

A solid-state detector pursuant to the present invention has numerous advantages in comparison with heretofore known solid-state gas detect units. A solid-state, multi-stage gas detector in accordance with the invention is suitable for monitoring contamination within an enclosure and provides improved reliability, sensitivity, selectivity, and installation and operation convenience than previous solid-state gas detectors. As one application, the detector is particularly suited for monitoring contamination within wafer transport and storage enclosures used in the semiconductor industry. Every wafer enclosure could have a detector continuously monitoring to detect small quantities of contaminants without interference from other gaseous species within the enclosure. A detector pursuant to the invention is easy to use and requires minimal or no maintenance. Applications for the multi-stage gas detector can be found throughout the semiconductor industry, along with the automotive, pharmaceutical and chemical industries, and the health care and environmental fields.

Although specific embodiments of the present invention have been illustrated in the accompanying drawings and described in the foregoing detailed description, it will be understood that the invention is not limited to the particular embodiments described herein, but is capable of numerous rearrangements, modifications and substitutions without departing from the scope of the invention. The following claims are intended to encompass all such modifications.

We claim:

1. A solid-state, multi-level gas detector for detecting at least one selected gaseous species of a plurality of gaseous species within an environment, said multi-level gas detector comprising:
   a first conductive layer exposable to the environment having the plurality of gaseous species, said first conductive layer permitting the at least one selected gaseous species to diffuse therethrough, and said first conductive layer interacting with at least one of the plurality of gaseous species within said environment such that conductivity thereof changes in response thereto;
   a second conductive layer electrically isolated from said first conductive layer and disposed to receive said at least one selected gaseous species after diffusing through said first conductive layer, said second conductive layer interacting with said at least one selected gaseous species such that conductivity thereof changes in response thereto; and
   electrical contact means electrically connected to said first conductive layer and to said second conductive layer for separately detecting conductivity change in said first conductive layer and conductivity change in said second conductive layer, said conductivity changes representing detection information for said at least one selected gaseous species.

2. The multi-level gas detector of claim 1, wherein said detector provides detection information for at least two selected gaseous species of said plurality of gaseous species within said environment, and wherein said first conductive layer permits at least one of said at least two selected gaseous species to diffuse therethrough, and said first conductive layer interacts with at least one of said at least two selected gaseous species such that conductivity thereof changes in response thereto.

3. The multi-level gas detector of claim 1, wherein said second conductive layer is located at least partially below said first conductive layer to facilitate said second conductive layer's contacting of said at least one selected gaseous species after said at least one selected gaseous species diffuses through said first conductive layer.

4. The multi-level gas detector of claim 1, wherein said first conductive layer filters at least one of said plurality of gaseous species from passing to said second conductive layer.

5. The multi-level gas detector of claim 4, wherein said one of said plurality of gaseous species affecting conductivity of said first conductive layer comprises said at least one selected gaseous species diffusing therethrough.

6. The multi-level gas detector of claim 1, wherein said one of said plurality of gaseous species affecting conductivity of said first conductive layer comprises a different one of said plurality of gaseous species than said at least one selected gaseous species diffusing therethrough.

7. The multi-level gas detector of claim 1, further comprising an electrical insulating layer disposed between said first conductive layer and said second conductive layer, said at least one selected gaseous species diffusing through said first conductive layer also diffusing through said electrical insulating layer before reaching said second conductive layer.

8. The multi-level gas detector of claim 1, wherein at least two selected gaseous species of said plurality of gaseous species within said environment diffuse through said first conductive layer, said second conductive layer being disposed to contact said at least two selected gaseous species and having a conductivity which changes in response to at least one of said at least two selected gaseous species, and wherein said multi-level gas detector further comprises a third conductive layer electrically isolated from said first conductive layer and said second conductive layer and disposed to contact at least one of said at least two gaseous species diffusing through said first conductive layer, said at least one of said at least two selected gaseous species reaching said third conductive layer interacting with said third conductive layer such that conductivity thereof changes in response thereto, said conductivity changes representing detection information for said at least two selected gaseous species.

9. The multi-level gas detector of claim 8, wherein said at least one of said at least two selected gaseous species reaching said third conductive layer contacts said third conductive layer after diffusing through said second conductive layer.

10. The multi-level gas detector of claim 9, wherein said second conductive layer is disposed at least partially in parallel opposing relation to said first conductive layer and said third conductive layer is disposed at least partially in parallel opposing relation to said second conductive layer.

11. The multi-level gas detector of claim 10, further comprising a first electrical insulating layer and a second electrical insulating layer, said first electrical insulating layer being disposed between said first conductive layer and said second conductive layer and said second electrical insulating layer being disposed between said second conductive layer and said third conductive layer, said first electrical insulating layer and said second electrical insulating layer each being at least partially semi-permeable to certain gaseous species.

12. The multi-level gas detector of claim 1, wherein said first conductive layer interacts with said at least one of the plurality of gaseous species by adsorption or absorption, and wherein said second conductive layer interacts with said at least one selected gaseous species by adsorption or absorption.

13. A solid-state, multi-level gas detector having multiple stages arranged in a stack configuration, said gas detector for detecting at least one selected gaseous species of a plurality of gaseous species within an environment, said gas detector comprising:

a first conductive layer exposable to the environment having the plurality of gaseous species, said first conductive layer permitting the at least one selected gaseous species to diffuse therethrough, and said first conductive layer interacting with at least one of the plurality of gaseous species within the environment such that conductivity of said first conductive layer changes in response thereto;

a second conductive layer isolated from said first conductive layer and disposed at least partially beneath said first conductive layer to contact said at least one selected gaseous species after said at least one selected gaseous species diffuses through said first conductive layer, said second conductive layer interacting with said at least one selected gaseous species such that conductivity of said second conductive layer changes in response thereto;

an electrical insulating layer disposed between said first conductive layer and said second conductive layer for electrically isolating said first conductive layer and said second conductive layer, said electrical insulating layer being at least semi-permeable such that said at least one selected gaseous species diffusing through said first conductive layer passes through said electrical insulating layer to said second conductive layer; and electrical contact means electrically connected to said first conductive layer and to said second conductive layer for separately detecting conductivity change in said first conductive layer and conductivity change in said second conductive layer, said conductivity changes representing detection information for said at least one selected gaseous species.

14. The multi-level gas detector of claim 13, wherein said second conductive layer is disposed completely below said first conductive layer in a plane substantially horizontal with the first conductive layer and extends beyond said first conductive layer in a direction parallel to said first conductive layer such that said at least one selected gaseous species diffusing through said first conductive layer contacts said second conductive layer and such that said first conductive layer and said second conductive layer form a pyramidal configuration.

15. The multi-level gas detector of claim 13, wherein said detector provides detection information for at least two selected gaseous species of said plurality of gaseous species within said environment, and wherein said at least two selected gaseous species diffuse through said first conductive layer, said second conductive layer contacting said at least two selected gaseous species and having a conductivity which changes in response to at least one of said at least two selected gaseous species, and wherein said multi-level gas detector further comprises a third conductive layer electrically isolated from the first conductive layer and the second conductive layer and disposed to contact at least one of said at least two gaseous species diffusing through the first conductive layer, said at least one of said at least two selected gaseous species reaching the third conductive layer interacting with said third conductive layer such that conductivity thereof changes in response thereto, said conductivity changes representing detection information for said at least two selected gaseous species.

16. The multi-level gas detector of claim 15, wherein said at least one of said at least two selected gaseous species received by said third conductive layer diffuses through said second conductive layer before reaching said third conductive layer.

17. The multi-level gas detector of claim 16, wherein said second conductive layer is disposed beneath said first conductive layer in a plane parallel to a plane of said first conductive layer and wherein said third conductive layer is disposed beneath said second conductive layer in a plane parallel to the plane of said second conductive layer.

18. The multi-level gas detector of claim 17, wherein said second conductive layer extends horizontally beyond said first conductive layer and wherein said third conductive layer extends horizontally beyond said second conductive layer such that a pyramidal stack configuration is formed by said first conductive layer, said second conductive layer and said third conductive layer.

19. The multi-level gas detector of claim 17, wherein said electrical insulating layer disposed between said first conductive layer and said second conductive layer comprises a first electrical insulating layer, and wherein a second electrical insulating layer is disposed between said second conductive layer and said third conductive layer for electrically isolating said second conductive layer and said third conductive layer, said second electrical insulating layer being at least semi-permeable.

* * * * *